(12) United States Patent
Kelly

(10) Patent No.: US 10,473,033 B2
(45) Date of Patent: Nov. 12, 2019

(54) GAS TURBINE ENGINE

(71) Applicant: HONEYWELL INTERNATIONAL INC., Morris Plains, NJ (US)

(72) Inventor: Jeff M. Kelly, Phoenix, AZ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 481 days.

(21) Appl. No.: 15/297,509

(22) Filed: Oct. 19, 2016

(65) Prior Publication Data

US 2018/0106196 A1 Apr. 19, 2018

(51) Int. Cl.
| F02C 7/266 | (2006.01) |
| B03C 1/28 | (2006.01) |
| F01D 25/18 | (2006.01) |
| F16N 29/04 | (2006.01) |
| G01N 15/10 | (2006.01) |

(52) U.S. Cl.
CPC .............. *F02C 7/266* (2013.01); *B03C 1/28* (2013.01); *F01D 25/18* (2013.01); *F16N 29/04* (2013.01); *G01N 15/1031* (2013.01); *F05D 2260/98* (2013.01); *F05D 2260/99* (2013.01); *Y02T 50/671* (2013.01)

(58) Field of Classification Search
USPC .................................. 361/232, 243–256, 435
See application file for complete search history.

(56) References Cited

U.S. PATENT DOCUMENTS

| 4,070,660 A | 1/1978 | Tauber |
| 4,219,805 A | 8/1980 | Magee et al. |
| 5,155,437 A * | 10/1992 | Frus .................. F02C 7/266 |
| | | 324/380 |
| 5,245,252 A * | 9/1993 | Frus .................. F02P 3/0869 |
| | | 123/634 |
| 5,406,208 A * | 4/1995 | Bitts .................. G01R 31/2836 |
| | | 180/338 |
| 5,742,234 A | 4/1998 | Owen |
| 5,936,830 A | 8/1999 | Rousseau et al. |
| 6,670,777 B1 * | 12/2003 | Petruska ............. F02P 3/0876 |
| | | 123/598 |

(Continued)

FOREIGN PATENT DOCUMENTS

FR   2681699 A   8/1980

OTHER PUBLICATIONS

Extended EP Search Report for Application No. 17196717.7 dated Mar. 15, 2018.

(Continued)

*Primary Examiner* — Tuan T Dinh

(74) *Attorney, Agent, or Firm* — Lorenz & Kopf, LLP

(57) ABSTRACT

An energy generation system for generating energy to be supplied to a chip zapping unit of for example a gas turbine engine comprises an ignition system, e.g. that of the gas turbine engine, the ignition system having an energy output and configured to supply operational energy to the energy output, and the chip zapping unit having an energy input, the energy input coupled to the energy output of the ignition system to receive the operational energy therefrom. Such an energy generation system generates the operational energy needed for the chip zapping unit directly from the ignition system thus avoiding pulse generation circuitry inside an electronic control unit.

8 Claims, 6 Drawing Sheets

(56) References Cited

U.S. PATENT DOCUMENTS

| | | | | |
|---|---|---|---|---|
| 7,355,300 B2* | 4/2008 | Wilmot | ............... | F02P 15/003 |
| | | | | 257/E29.216 |
| 2003/0067284 A1* | 4/2003 | Costello | ............... | F02C 7/266 |
| | | | | 322/59 |
| 2005/0172637 A1* | 8/2005 | Ponziani | ............... | F02C 7/266 |
| | | | | 60/776 |
| 2005/0276000 A1* | 12/2005 | Wilmot | ............... | F02P 15/003 |
| | | | | 361/247 |
| 2015/0260107 A1* | 9/2015 | Wright | ............... | F02C 7/266 |
| | | | | 315/210 |

OTHER PUBLICATIONS

Eaton Aerospace, "Eaton: Smart Zapper System", Dec. 23, 2005, ZP055457029.

* cited by examiner

GAS TURBINE ENGINE

TECHNICAL FIELD

The present invention generally relates to gas turbine engines and more particularly relates to a chip zapping unit employed in a lubrication system of the gas turbine engine for removing metal parts from the lubrication fluid and even more particularly to an energy generation system and method for generating the operational energy needed by the chip zapping unit.

BACKGROUND

A typical gas turbine engine includes at least a compressor section, a combustion section and a turbine section. In the compressor section and in the turbine section typically lubrication fluids are necessary. Lubrication may also be necessary in other parts of the gas turbine engine or even in an aircraft which is powered by the gas turbine engine, for example in the transmission or gearbox of a helicopter. During prolonged operation metal chips may accumulate in the transmission fluid or lubrication fluid. The metal chips may be generated during normal operation (despite the presence of the lubrication fluid) as a result of grinding processes between moving parts, in particular metal parts such as transmission gears. Furthermore, a significant number of metal chips in the transmission fluid can also indicate general mechanical problems with a transmission.

Metal particles in a lubrication system are undesirable. As such, many gas turbine engines are typically equipped with a chip zapping unit (also called a "chip zapper"), which not only detects the presence of the metal particles, but also attracts them to a side surface of the lubrication system. Depending on the application, some chip zapping units also burn the metal particles to clean the lubrication fluid. For example, when a chip enters a chip detector, a capacitor is discharged through the chip to heat and burn away the unwanted particles or chips.

The chip zapper is typically immersed in the lubrication fluid together with the chip detector. The chip zapper in the magnetically attracts, for example, ferromagnetic particles suspended in the fluid. As a result, the chip detector contacts will be bridged by the particles such that the detector can issue a warning about the presence of particles in the lubrication oil systems of the aircraft or the gas turbine engine. When the warning is issued, the lubrication oil can be replaced.

The chip zapping unit (chip zapper) typically has an energy input to receive operational energy. Typically, the chip zapper in a typical control system on gas turbine engines receives electrical pulses generated by the electronic control unit (ECU) of the gas turbine engine. The electronic control unit is the central control system which receives energy from typically a permanent magnet alternator provided on a rotational shaft of the turbine or the compressor. However, in order for the chip zapper to perform its function of attracting metal particles in the lubrication fluid, the ECU must provide relatively high energy. As may be appreciated, the circuits necessary for this generally increase the footprint inside an ECU that is already challenged for space. Furthermore, such high energy power generation inside the ECU can result in additional costs to the ECU and decrease the overall reliability of the ECU. Furthermore, since the ECU has to supply pulses of energy which are sufficient to "zap" any of the metallic particles on the chip detector, the electrical harnesses that connect the ECU and the chip detector/zapper need to fulfil specific design criteria for the pulses that are unique for the gas turbine engine harness (harnesses). For example, such harnesses increase the likelihood of electromagnetic interference and lightning threats in the energy generation system. Furthermore, the energy generation unit inside the electronic control unit needs to be shielded efficiently from other parts of the electronic control unit that may be operating at much lower voltage than that needed for generating the high energy pulses for the chip zapper. Therefore, generating the high energy pulses for the chip zapper inside the electronic control unit also presents potential challenges if high energy and low energy control units are arranged close to each other in the limited space of the ECU.

Thus, while presently known electronic control units and chip zappers are generally safe, reliable and robust, gas turbine engines with an electronic control unit including an energy generation unit for generating operational energy for the chip zapper can exhibit the above described drawbacks, in particular a large footprint inside the ECU, and increased weight due to the additional circuits in the electronic control unit and the potential challenges of electromagnetic interference and interaction as well as lightning threats.

Hence, there is a need for a gas turbine engine having an electronic control unit that uses relatively less components and/or occupies less space and/or weights than existing systems and which nevertheless guarantees that the chip zapping unit is supplied with sufficient operational energy for attracting the metal particles in the lubrication oil system. The present invention addresses one or more of these needs. In particular, the present invention aims at providing a system and a method for efficiently generating operational energy to be supplied to the chip sapping unit of a gas turbine engine.

BRIEF SUMMARY

In one embodiment, an energy generation system of a gas turbine engine comprises an ignition system, the ignition system having an energy output and configured to supply operational energy to the energy output, and a chip zapping unit having an energy input, the energy input coupled to the energy output of the ignition system to receive the operational energy therefrom.

In another embodiment a method for generating operational energy to be supplied to a chip zapping unit of a gas turbine engine comprises the steps of generating the operational energy using an ignition system of the gas turbine engine, and supplying the operational energy generated by the ignition system to the chip zapping unit of the gas turbine engine.

In another embodiment the energy generation system of a gas turbine engine for generating operational energy for a chip zapping unit comprises an ignition system, the ignition system comprising an ignition igniter having an ignition gap, and an ignition exciter coupled to the ignition igniter, the ignition exciter comprising shunt circuitry, the shunt circuitry connected parallel to the ignition gap and coupled to the chip zapping unit.

According to these embodiments of the invention, the technical problem of energy generation inside the electronic control unit for the chip zapper on gas turbine engines is solved. That is, according to the embodiments of the invention, excess energy that is stored in the ignition exciter and discharged to the ground plane when the ignition exciter is commanded off is used as operational energy for driving the chip zapping unit. This replaces the space intensive energy generation units and their electrical circuitry inside the electronic control unit. Therefore, according to the embodiments of the invention no additional energy generation units are needed, neither in the electronic control unit nor elsewhere in the gas turbine engine because the somewhat wasted energy already present during discharge in the ignition exciter is used as operational energy for the chip zapping unit. Furthermore, the electromagnetic interference problem inside the electronic control unit is solved because high and low energy units are not placed next to each other.

Further advantageous features and improvements of the invention will become apparent from the subsequent detailed description and the appended claims, taken in conjunction with the accompanying drawings and the preceding background.

BRIEF DESCRIPTION OF THE DRAWINGS

Hereinafter, the present invention will be described in conjunction with the following drawing figures in which similar reference numerals denote similar elements or steps. In the drawings:

FIG. 3-1 shows a functional block diagram of the energy generation method for supplying energy to a chip zapping unit in accordance with the principle of the invention;

FIG. 3-2 shows a functional block diagram of FIG. 3-1 with further details;

FIG. 3-3 shows a concrete embodiment of the energy generation system in accordance with the invention;

FIG. 3-4 shows a preferred electronic control unit ECU employing a rectifying unit for generating DC energy;

FIG. 4-1 shows a flowchart of energy generation for a chip zapper in accordance with the principle of the invention;

FIG. 4-2 shows another flowchart of energy generation in accordance with another embodiment of the invention;

FIG. 5-1 shows a functional block diagram of an ignition system of the gas turbine engine;

FIG. 5-2 depicts a schematic diagram of an embodiment of the shunt circuitry shown in FIG. 3-2; and FIG. 5-3 shows an embodiment of further details of the ignition system and the ignition exciter.

DETAILED DESCRIPTION

Hereinafter, embodiments of the present invention are described with reference to the attached drawings. However, it should be noted that the following detailed description is merely exemplary in nature and is not intended to limit the invention or the application and uses of the invention. As used herein, the word "exemplary" means "serving as an example, instance, or illustration". Thus, any embodiment described herein as "exemplary" is not necessarily to be construed as preferred or advantageous over other embodiments. All the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary of the following detailed description.

Figure 1:
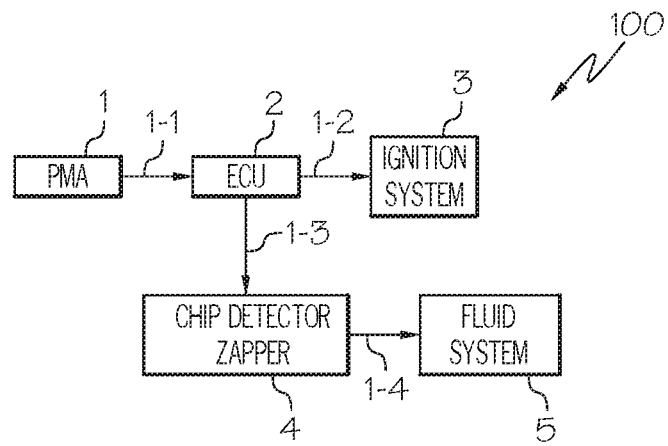
FIG. 1 shows a functional block diagram of a conventional system for supplying pulse energy to a chip detector/zapper.

Referring now to FIG. 1, a functional block diagram of details of a conventional operational energy generation system 100 for a chip zapper in a gas turbine engine is depicted with particular emphasis on how the operational energy is generated for a chip detector/zapper denoted with reference numeral 4. Typically, the operational energy generation system 100 in FIG. 1 comprises a permanent magnet alternator 1 which typically generates AC energy to be supplied to an electronic control unit (ECU) 2. The ECU 2 is a separate unit attached to the gas turbine engine and it generates DC energy supplied through a harness 1-2 to the ignition system 3. As explained above, the conventional electronic control unit 2 comprises chip zapping unit operational energy generation circuitry inside and supplies electrical pulses through a harness 1-3 to the chip detector/zapper 4. The chip detector/zapper couples to the fluid system 5, typically a lubrication oil system.

Figure 2:
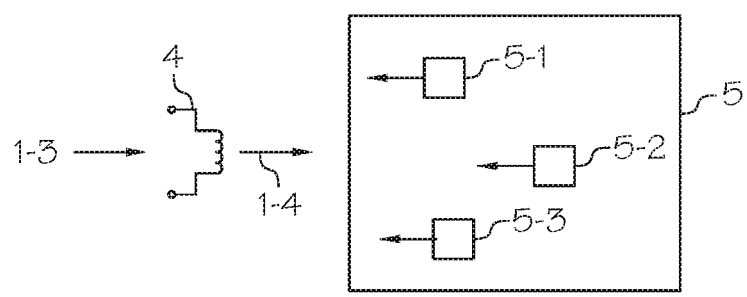
FIG. 2 shows a schematic diagram of the operation of a chip zapper.

As shown in FIG. 2, the chip zapping unit 4 is typically an electromagnet which receives pulses 1-3 from the electronic control unit ECU and attracts metal particles 5-1, 5-2, 5-3 that may be present in the lubrication system 5. As also explained above, typically, the chip zapping unit 4 cooperates with a chip detector which detects the presence of such metallic particles 5-1, 5-2, 5-3.

In the conventional operational energy generation system in FIG. 1 and FIG. 2, as already partially described above, the footprint inside the conventional electronic control unit 2 is already very challenged for space. Furthermore, the electrical harness 1-3 that connects the ECU and the chip detector/zapper requires a specific design for the pulses that are unique for the gas turbine engine harnesses. Furthermore, since quite substantial energy is needed for driving the chip detector/zapper 4, there may be also thermal problems inside the conventional electronic control unit, in addition to potential electromagnetic interference (EMI) and lightning problems.

Figures 1, 3:
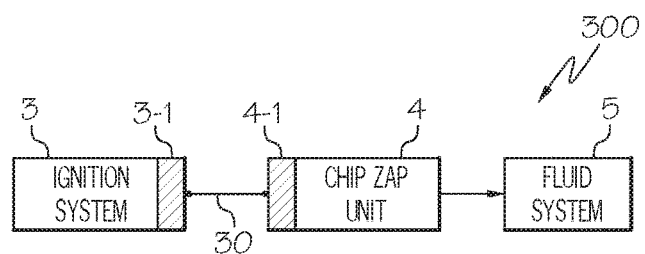
Figures 2, 3:
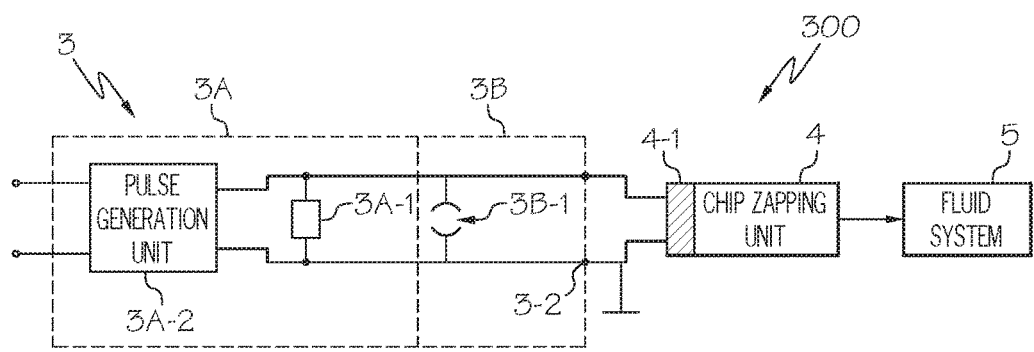
Figure 3:
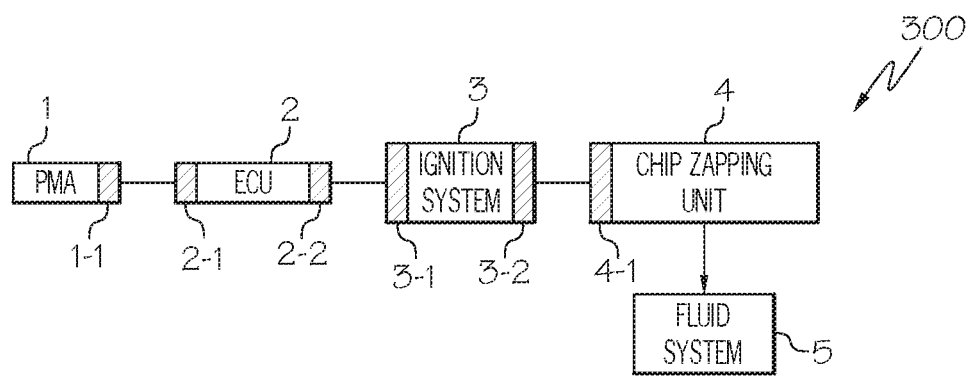

FIG. 3-1 shows an energy generation system 300 for generating operational energy for a chip zapping unit in accordance with one embodiment. The energy generation system 300 comprises an ignition system 3 having an energy output 3-1 and configured to supply operational energy 30 to the energy output 3-1. The chip zapping unit 4 has an energy input 4-1 which is coupled to the energy output 3-1 of the ignition system 3. The energy input 4-1 of the chip zapping unit 4 receives the operational energy 30 from the ignition system 3. Therefore, in contrast to the conventional system in FIG. 1, the energy generation system depicted in FIG. 3-1 does not require any circuitry inside the electronic control unit. As shown in FIG. 3-1, the energy is directly taken from the ignition system 3 and, as will be seen below, there are also no additional energy generation circuits necessary inside the ignition system 3. As in FIG. 1, the chip zapping unit 4 in FIG. 3-1 is coupled to the fluid system 5 and is configured to attract metal particles, possibly in combination with a chip detector.

Figures 3, 4:
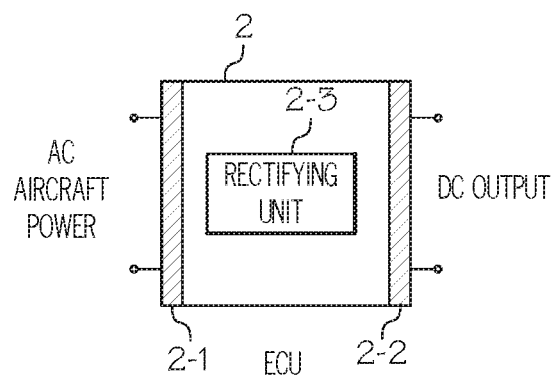
Figures 1, 4:
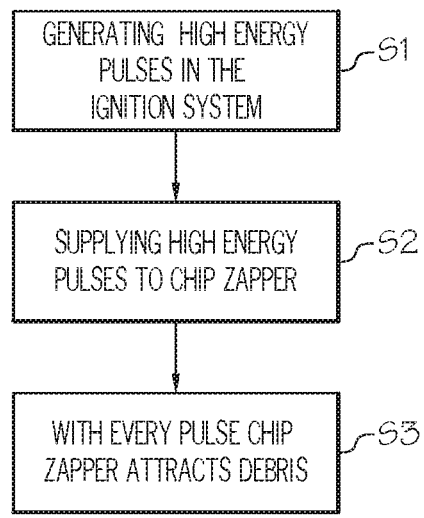
Figures 2, 4:
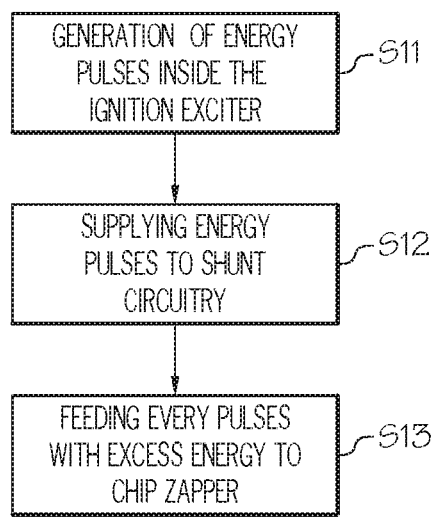

The method for generating operational energy to be supplied to the chip zapping unit 4, 4-1 of the gas turbine engine in accordance with the one embodiment is shown in FIG. 4-1. In step S1 the operational energy is generated using the ignition system 3 of the gas turbine engine, as shown in FIG. 3-1. In step S2 the operational energy generated by the ignition system 3 is supplied to the chip zapping unit 4 of the gas turbine engine. Using the operational energy generated by the ignition system 3 the chip zapping unit 4 attracts debris in the lubrication oil system with every operational pulse supplied from the ignition system in step S3.

Therefore, in the unique energy generation system and method as shown in FIG. 3-1 and FIG. 4-1, the ignition system, and more particularly the ignition exciter as will be seen below, is the subsystem that delivers the operational energy to the chip zapping unit. Since the electronic control unit does not need additional circuitry to energize the chip zapper, the space and weight problems are solved. Furthermore, there are also no electromagnetic interference problems in the ECU since the ECU does not comprise the energy generation unit for the chip zapper. Since the electromagnetic interference problems are at least diminished, the electronic control unit is also more reliable and can also be manufactured at lower cost.

FIG. 3-2 shows an embodiment of the functional block diagram in FIG. 3-1. The ignition system 3 shown in FIG. 3-2 comprises an ignition igniter 3B having an ignition gap 3B-1. Typically, the ignition igniter 3B is a discharge tube which generates an electric discharge when a high voltage is supplied causing a breakdown of the air gap between the two electrodes. The ignition system 3 in FIG. 3-2 further comprises an ignition exciter 3A coupled to the ignition igniter 3B. The ignition exciter 3A typically comprises a shunt circuitry 3A-1 wherein the shunt circuitry 3A-1, as shown in FIG. 3-2, is connected parallel to the ignition gap 3B-1 and is also coupled to the chip zapping unit 4 at its energy input 4-1.

FIG. 3-2 shows an advantageous embodiment including a pulse generation unit 3A-2. The pulse generation unit 3A-2, as just explained, generates the high energy pulses to cause the breakdown of the air gap of the ignition igniter to generate the ignition spark, similar to a spark plug on an internal combustion engine. That is, the ignition exciter 3A creates the charge that is sent to the ignition igniter 3B to cause the discharge. However, in addition to the traditional requirements of an ignition exciter 3A to generate the high discharge electrical pulse, the ignition exciter 3A has an electrical output to the chip zapper 4 which is the shunt circuitry 3A-1 inside the ignition exciter 3A. The electrical output is designated with reference numeral 3-2 in FIG. 3-2.

Thus, as shown in the flowchart of FIG. 4-2, the pulse generation unit 3A-2 inside the ignition system 3 generates energy pulses in step S11. In step S12 the energy pulses are supplied to the shunt circuitry 3A-1 and in step S13 the supplied energy pulses with the excess energy is supplied to the chip zapping unit 4. Hence, by having the chip zapping unit 4 coupled to the ignition igniter 3B having the shunt circuitry 3A-1 and the electrical output 3-2, excess energy that is stored in the ignition exciter and is conventionally discharged to the ground plane when the ignition exciter 3A is commanded off can instead be used as electrical pulses for driving the chip zapping unit 4. Hence, using this excess energy replaces the electrical circuitry inside the conventional electronic control unit. The shunt circuitry 3A-1 discharges the energy to the ground plane each time the ignition exciter 3A is turned off.

The shunt circuitry 3A-1 ensures that personnel working on the engine do not come into contact with a spark from the ignition exciter 3A. However, it was realized that the shunt circuitry energy during discharge is effectively wasted energy as it is discharged to the ground plane in conventional systems. By connecting the ignition exciter output to the shunt circuitry 3A-1, this energy is used for the chip zapping unit each time the ignition exciter 3A is powered off. Thus, the technical problems associated with energy generation inside the electronic control unit, such as additional cost, space requirements and reliability of the ECU are solved. Furthermore, since there is no energy generation inside the ECU, no negative thermal effects or electromagnetic interference problems and lighting threats exist. The embodiments disclosed herein also do not require sophisticated software and hardware in the ECU to determine a chip of a required size to be present on the chip detector. It will be zapped and effectively cleaned every time the ignition system is turned off. The embodiments disclosed herein can be used with a conventional ignition system, with no need for substantial modifications. It is only necessary to connect an electrical connector 3-2 to the shunt circuitry 3A-1 that is already provided inside the ignition system and more particularly in the ignition exciter 3A. Such an electrical connector can be typically a military style electrical connector.

FIG. 3-3 shows an embodiment of the energy generation system 300 with further details. It encompasses the ignition system 3 having an energy input 3-1 connected to an energy output 2-2 of an electronic control unit 2, which in turn has an energy input 2-1 coupled to an energy output 1-1 of an energy generation unit 1 that is configured to supply operational energy. An example of the energy generation unit 1 is a permanent magnet alternator, as already mentioned above. The energy input 2-1 of the electronic control unit 2 is coupled to the energy output 2-2 of the energy generation unit 1, and the energy output 2-2 of the electronic control unit 2 is coupled to the energy input 3-1 of the ignition system 1. Typically, the energy generation unit 1 is configured to output AC operational energy to the energy input 2-1 of the electronic control unit 2, and the electronic control unit 2 may preferably comprise energy rectification circuitry 2-3.

The rectification circuitry 2-3, which is depicted in FIG. 3-4, is configured to rectify the AC operational energy received from the permanent magnet alternator 1 into DC operational energy. That is, the ignition system 3 may receive DC operational energy generated by the electronic control unit 2. The energy output 2-2 of the electronic control unit 2 is coupled to supply the DC operational energy to the energy input 3-1 of the ignition system 3. As can be seen from FIG. 3-3 and FIG. 3-4, no additional circuitry except for the energy rectification circuitry 2-3 is necessary inside the electronic control unit 2. The chip zapping unit 4 directly receives the required pulse energy (electrical energy pulses) from the ignition system 3, more particularly from the connector 3-2 coupled to the shunt circuitry 3A-1 as shown in FIG. 3-2.

Figures 1, 5:
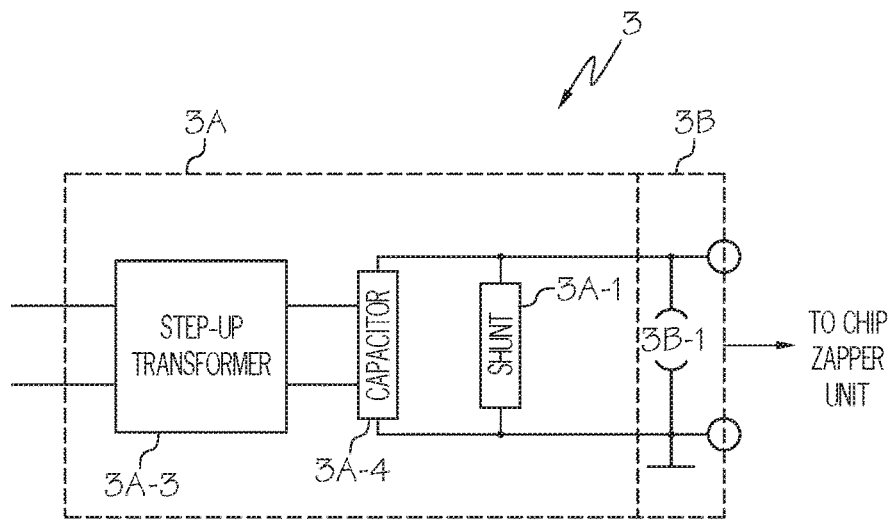
Figures 2, 5:
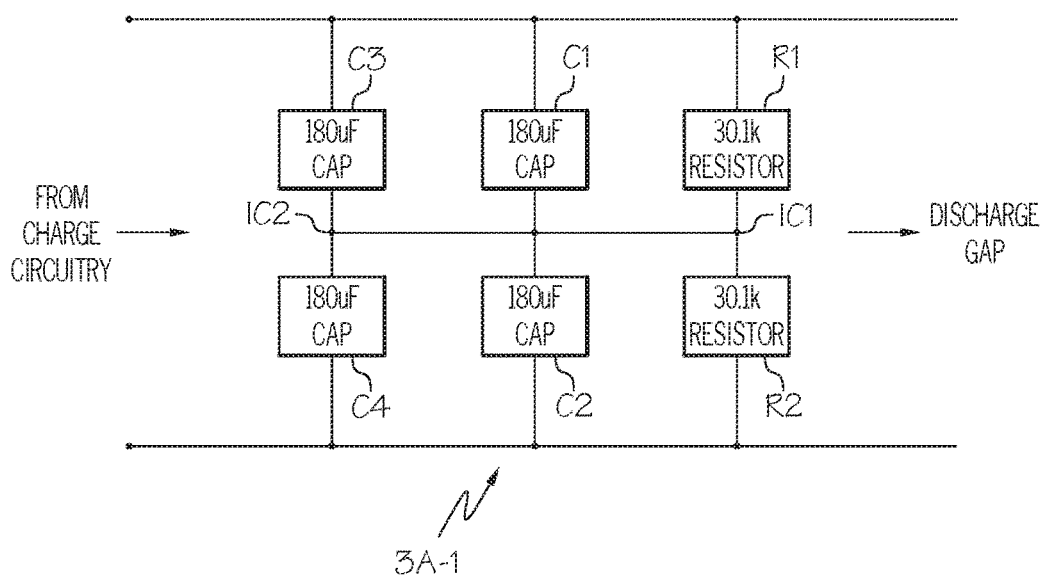
Figures 3, 5:
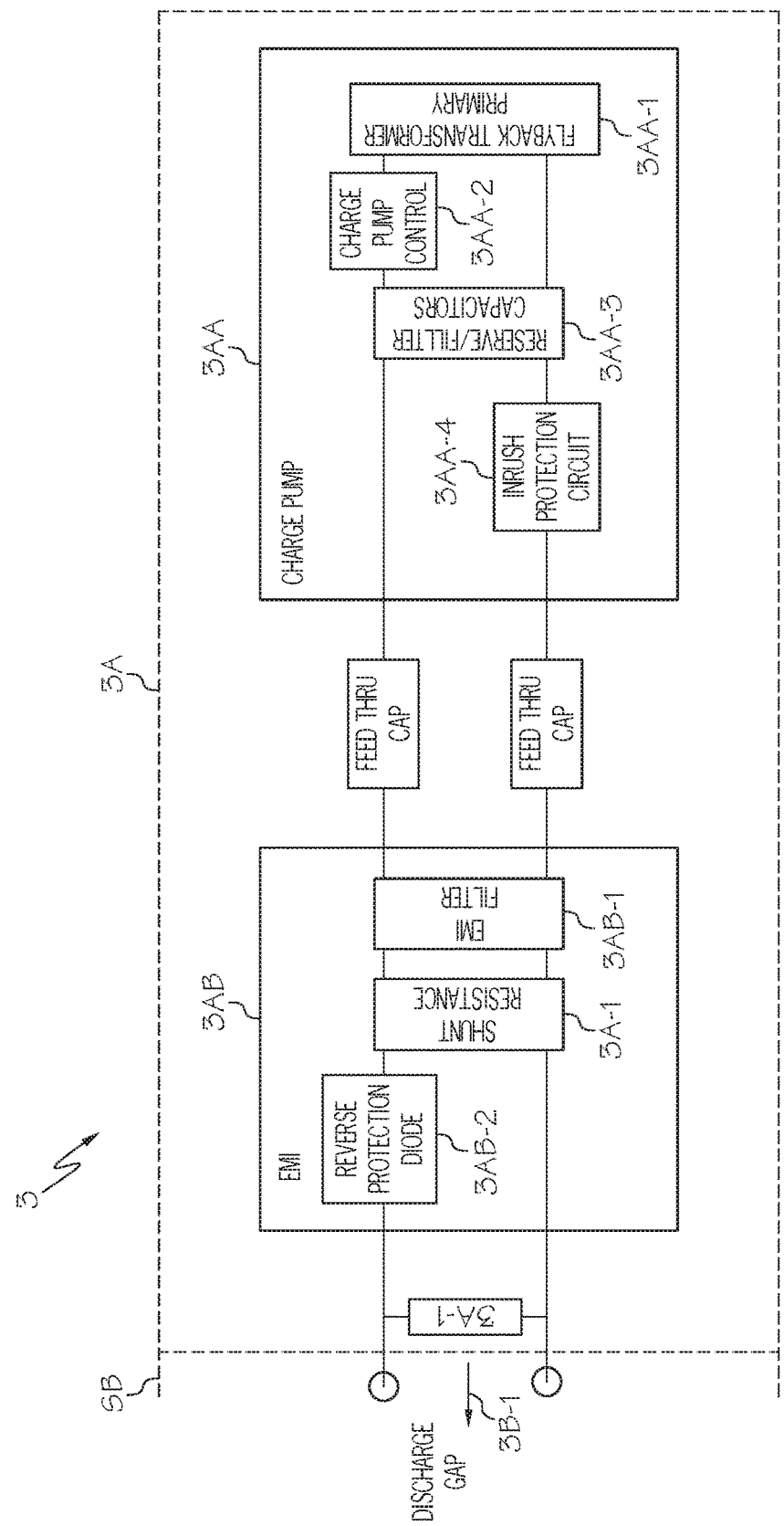

FIG. 5-1 shows an embodiment of the ignition system 3 with further details. FIG. 5-1 does not only show a block diagram of the shunt circuitry 3A-1 inside the ignition exciter 3A but also the unit for generating the electrical pulses which cause the breakdown of the air gap (the ionization of the air gap 3B-1). Typically, inside the ignition system 3, the pulse generation unit 3A-2 shown in FIG. 3-2 comprises a step-up transformer 3A-3 which charges a capacitor bank 3A-4 coupled to the shunt circuitry 3A-1. FIG. 5-1 shows an ignition system 3 where the electrical pulses for the ignition igniter 3B are generated from the AC energy that is supplied from the electronic control unit 2 as shown in the FIG. 3-3. The basic principle of generating the electrical energy pulses for the ionization of the spark gap 3B-1 is based on stepping up the voltage to a higher level, and then storing the energy in the capacitor bank 3A-4 until the breakdown of the air gap 3B-1 occurs generating an electrical pulse, that is excess energy will be generated in the shunt circuitry 3A-1.

A typical block diagram of the shunt circuitry 3A-1 is shown in FIG. 5-2. That is, the shunt circuitry 3A-1 comprises parallel connections of at least a first serial connection of two capacitors C1, C2, and a second serial connection of two capacitors C3, C4, which are interconnected at a circuit node #. The depicted shunt circuitry also includes a serial connection of two resistors R1, R2, which are also interconnected at the circuit node #. It will be appreciated by a skilled person in the art that the shunt circuitry 3A-1 may be extended to comprise a larger number of parallel connections of resistors and capacitors than what is shown in FIG. 5-2.

A more detailed block diagram of the circuits shown in FIG. 5-1 is shown in FIG. 5-3. The ignition system 3 in FIG. 5-3 comprises as principal blocks a charge pump circuit 3AA and an electromagnetic interference (EMI) circuit 3AB coupled by feed thru capacitors. Shown in FIG. 5-3 is also the shunt circuitry 3A-1. The charge pump 3AA comprises a flyback transformer 3AA-1, a charge pump control circuit 3AA-2, filter capacitors 3AA-3 and an inrush protection circuit 3AA-4. The EMIC circuit 3AB can comprise an EMI filter 3AB-1, shunt resistance 3A-1 as already described and a reverse protection diode 3AB-2. As principally explained with reference to FIG. 5-1, the charge pump 3AA will generate pulse energy fed through the EMI filter parallel to the shunt circuitry 3A-1 and to the discharge gap 3B-1. Various versions of the charge pump 3AA are possible and FIG. 5-3 shows one which operates with received AC energy.

A further advantageous embodiment can comprise an energy regulation circuit regulating the operational energy to the chap zapping unit 4 inside the ignition exciter 3A. That is, as shown in FIG. 3-2 (and as can be understood from FIG. 5-1 and FIG. 5-3), the chip zapping unit 4 may receive its operational energy directly from an (e.g. military style) electrical connector 3-2 parallel to the shunt circuitry 3A-1. This means, that the chip zapping unit 4 may receive directly the energy generated during discharge, namely the ignition exciter shunt circuitry wasted energy that is discharged to the ground plane in the system during discharge. However, an energy regulation circuit can be used between the chap zapping unit 4 and the electrical connector 3-2 inside the ignition exciter 3A or the ignition igniter 3B such that the chap zapping unit 4 is provided with an adjusted or regulated operational energy. That is, there may even be a step-up transformer between the shunt circuitry 3A-1 and the chip zapping unit 4 stepping up the voltage to generate a pulse with higher energy. Depending on the specifications of the chip zapping unit 4, for example an electromagnet, it may also be possible that the regulation circuit steps-down the level of operational energy generated by the shunt circuitry 3A-1 during discharge.

With the described energy generation system for generating operational energy for a chip zapping unit in accordance with the invention, there is no need for any additional circuitry in the electronic control unit which can thus be fabricated with a smaller footprint and lower weight and cost. The present invention uses the excess energy which is anyway present during discharge over the shunt circuitry such that also in the ignition system itself no additional circuits will be necessary. The described system additionally enhances electromagnetic interference measures and thermal problems conventionally existing in the electronic control unit of the prior art.

In this document, relational terms such as first and second and the like may be used solely to distinguish one entity or action from another entity or action without necessarily requiring or implying any actual such relationship or order between such entities or actions. Numerical ordinals such as "first", "second", "third", etc. simply denote different singles of a plurality and do not imply any order or sequence unless specifically defined by the claim language. The sequence of the text in any of the claims does not imply that process steps must be performed in a temporal or logical order according to such a sequence unless it is specified specifically by the language of the claim. Therefore, the process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be coupled to each other physically, electronically, logically or in any other manner, through one or more additional elements.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing," or any other variation thereof, are intended to cover a non-exclusive inclusion, such that a process, method, article, or arrangement that comprises, has, includes, contains a list of elements does not include only those elements, but may include other elements not expressly listed or inherent to such process, method, article, or arrangement. An element proceeded by "comprises . . . a," "has . . . a," "includes . . . a," or "contains . . . a," does not, without more constraints, preclude the existence of additional identical elements in the process, method, article, or arrangement that comprises, has, includes, or contains the element. The terms "a" and "an" are defined as one or more unless explicitly stated otherwise herein. The terms "substantially," "essentially," "approximately," "about," or any other version thereof, are defined as being close to as understood by one of ordinary skill in the art, and in one non-limiting embodiment the term is defined to be within 10%, in another embodiment within 5%, in another embodiment within 1%, and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

Furthermore, while at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability or configuration of the invention in any way. Much rather, the foregoing detailed description will provide those skilled in the art with a convenient roadmap for implementing an exemplary embodiment of the invention it being understood that various changes may be made in the function and arrangement of elements described in an exemplary embodiment without departing from the scope of the invention as set forth in the following appended claims.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. A gas turbine engine, comprising:
an ignition system, the ignition system having an energy output and that supplies operational energy, in the form of electrical energy pulses, to the energy output; and
a chip zapping unit having an energy input, the energy input coupled to the energy output of the ignition system to receive the operational energy therefrom,
wherein the ignition system comprises:
an ignition igniter having an ignition gap; and
an ignition exciter coupled to the ignition igniter, the ignition exciter comprising shunt circuitry, the shunt circuitry connected parallel to the ignition gap and coupled to the energy input of the chip zapping unit through the energy output of the ignition system, the ignition exciter further comprising a charge pump circuit and an electromagnetic interference (EMI) circuit, the charge pump circuit comprising a flyback transformer, a charge pump control circuit, filter capacitors, and an inrush protection circuit, the EMI circuit comprising an EMI filter, a shunt resistance, and a reverse protection diode.

2. The gas turbine engine of claim 1, wherein the ignition system further comprises an energy input, and wherein the gas turbine engine further comprises:
an energy generation unit having an energy output and that supplies operational energy; and
an electronic control unit having an energy input and an energy output, the energy input of the electronic control unit coupled to the energy output of the energy generation unit, the energy output of the electronic control unit coupled to the energy input of the ignition system.

3. The gas turbine engine of claim 1, wherein the chip zapping unit comprises an electromagnet coupled to receive the electrical energy pulses.

4. The gas turbine engine according of claim 1, wherein:
the ignition exciter further comprises an energy pulse generation unit that is adapted to generate energy pulses to be applied to an ignition igniter ignition gap, the energy of the energy pulses is excess energy stored in the ignition exciter and discharged to a ground plane by shunt circuitry each time the ignition exciter is turned off.

5. The gas turbine engine of claim 1, wherein the ignition exciter further comprises a regulation circuit for regulating the operational energy to the chip zapping unit.

6. The gas turbine engine of claim 2, wherein:
the energy generation unit is a permanent magnet alternator that outputs AC operational energy to the input unit of the electronic control unit;
the electronic control unit comprises energy rectification circuitry that rectifies the AC operational energy received from the permanent magnet alternator into DC operational energy; and
the energy output of the electronic control unit coupled to supply the DC operational energy to the energy input of the ignition system.

7. The gas turbine engine of claim 2, wherein the energy output of the ignition system is a military style electrical connector connected to the shunt circuitry of the ignition igniter.

8. A gas turbine engine, comprising:
an ignition system, the ignition system having an energy output and operable to supply operational energy, in the form of electrical energy pulses, to the energy output; and
a chip zapping unit having an energy input, the energy input coupled to the energy output of the ignition system to receive the operational energy therefrom,
wherein the ignition system comprises:
an ignition igniter having an ignition gap; and
an ignition exciter coupled to the ignition igniter, the ignition exciter comprising shunt circuitry, the shunt circuitry connected parallel to the ignition gap and coupled to the energy input of the chip zapping unit through the energy output of the ignition system, the ignition exciter further comprising a charge pump circuit and an electromagnetic interference (EMI) circuit, the shunt circuitry comprising a parallel connection of at least a first serial connection of two capacitors interconnected at a first serial connection node and a second serial connection of two resistors interconnected at a second serial interconnection node, the first and second interconnection nodes coupled to each other.

* * * * *